US006872275B2

(12) United States Patent
Ko et al.

(10) Patent No.: US 6,872,275 B2
(45) Date of Patent: *Mar. 29, 2005

(54) PROCESS FOR ADDING SUPERABSORBENT TO A PRE-FORMED FIBROUS WEB VIA IN SITU POLYMERIZATION

(75) Inventors: Young C. Ko, Neenah, WI (US); Stanley R. Kellenberger, Appleton, WI (US); David Martin Jackson, Roswell, GA (US); Dave A. Soerens, Neenah, WI (US); Jason M. Laumer, Appleton, WI (US); Sridhar Ranganathan, Suwanee, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 370 days.

This patent is subject to a terminal disclaimer.

(21) Appl. No.: 10/017,681

(22) Filed: Dec. 14, 2001

(65) Prior Publication Data

US 2003/0113463 A1 Jun. 19, 2003

(51) Int. Cl.⁷ .................................. B05D 1/36

(52) U.S. Cl. ................. 156/181; 156/277; 156/279; 427/337; 427/392; 427/393; 427/407.1; 264/109; 264/122

(58) Field of Search ............... 156/62.2, 180, 156/181, 279; 427/392, 393, 331, 337, 407.1; 264/109, 122

(56) References Cited

U.S. PATENT DOCUMENTS

| | | | |
|---|---|---|---|
| 3,338,992 A | 8/1967 | Kinney | |
| 3,341,394 A | 9/1967 | Kinney | |
| 3,502,538 A | 3/1970 | Petersen | |
| 3,502,763 A | 3/1970 | Hartmann | |
| 3,542,615 A | 11/1970 | Dobo et al. | |
| 3,692,618 A | 9/1972 | Dorschner et al. | |
| 3,802,817 A | 4/1974 | Matsuki et al. | |
| 3,849,241 A | 11/1974 | Butin et al. | |
| 3,901,236 A | 8/1975 | Assarsson et al. | |
| 4,076,663 A | 2/1978 | Masuda et al. | |
| 4,100,324 A | 7/1978 | Anderson et al. | |
| 4,151,130 A | 4/1979 | Adams | 260/17.4 GC |
| 4,286,082 A | 8/1981 | Tsubakimoto et al. | |
| 4,340,563 A | 7/1982 | Appel et al. | |
| 4,500,315 A | 2/1985 | Pieniak et al. | |
| 4,537,590 A | 8/1985 | Pieniak et al. | |
| 4,540,454 A | 9/1985 | Pieniak et al. | |
| 4,559,050 A | 12/1985 | Iskra | |
| 4,560,372 A | 12/1985 | Pieniak | |
| 4,596,567 A | 6/1986 | Iskra | |
| 4,605,402 A | 8/1986 | Iskra | |
| 4,676,784 A | 6/1987 | Erdman et al. | |
| 4,699,823 A * | 10/1987 | Kellenberger et al. | 428/219 |
| 4,818,464 A | 4/1989 | Lau | |
| 4,888,238 A | 12/1989 | Katz et al. | 428/378 |
| 4,892,754 A | 1/1990 | Itoh et al. | |
| 4,902,559 A | 2/1990 | Eschwey et al. | |
| 4,958,385 A | 9/1990 | Rushton, Jr. | 2/174 |
| 5,059,664 A | 10/1991 | Yada et al. | 526/240 |
| 5,071,681 A | 12/1991 | Manning et al. | 427/392 |
| 5,175,046 A | 12/1992 | Nguyen | 428/198 |
| 5,248,524 A | 9/1993 | Soderlund | 427/200 |
| 5,298,284 A | 3/1994 | Buckwald et al. | 427/203 |
| 5,300,565 A | 4/1994 | Berg et al. | 525/54.2 |
| 5,350,624 A | 9/1994 | Georger et al. | |
| 5,422,169 A * | 6/1995 | Roe | 428/212 |
| 5,454,801 A | 10/1995 | Lauritzen | 604/378 |
| 5,487,736 A | 1/1996 | Van Phan | 604/368 |
| 5,489,469 A | 2/1996 | Kobayashi et al. | 428/283 |
| 5,506,035 A | 4/1996 | Van Phan et al. | 428/196 |
| 5,547,747 A * | 8/1996 | Trokhan et al. | 428/320.2 |
| 5,549,928 A | 8/1996 | Trokhan et al. | |
| 5,620,742 A | 4/1997 | Lauritzen | 427/209 |
| 5,674,478 A | 10/1997 | Dodd et al. | |
| 5,817,081 A * | 10/1998 | LaVon et al. | 604/378 |
| 5,821,179 A * | 10/1998 | Masaki et al. | 442/375 |
| 5,868,724 A | 2/1999 | Dierckes, Jr. et al. | 604/368 |
| 5,875,967 A | 3/1999 | Ruth, III | |
| 5,962,068 A | 10/1999 | Tsuchiya et al. | |
| 5,998,312 A | 12/1999 | Kroesbergen | 442/221 |
| 6,019,457 A | 2/2000 | Silverbrook | |
| 6,022,610 A | 2/2000 | Phan et al. | |
| 6,024,438 A | 2/2000 | Koike et al. | |
| 6,043,311 A | 3/2000 | Houben et al. | 524/522 |
| 6,086,950 A | 7/2000 | Masaki et al. | |
| 6,103,061 A * | 8/2000 | Anderson et al. | 162/108 |
| 6,235,659 B1 | 5/2001 | McAmish et al. | 442/79 |
| 6,242,073 B1 | 6/2001 | Phan et al. | 428/132 |
| 6,417,425 B1 | 7/2002 | Whitmore et al. | |
| 6,533,989 B1 * | 3/2003 | Wisneski et al. | 264/510 |
| 2003/0149413 A1 | 8/2003 | Mechawej | 604/368 |
| 2003/0205318 A1 | 11/2003 | Ko et al. | |
| 2003/0211248 A1 | 11/2003 | Ko et al. | |

FOREIGN PATENT DOCUMENTS

| | | | | |
|---|---|---|---|---|
| DE | 199 05 947 A1 | 8/2000 | ........... | A61L/15/60 |
| EP | 0 022 792 B1 | 5/1984 | ........... | A61F/13/16 |
| EP | 0 290 814 A2 | 11/1988 | ........... | C08F/20/06 |
| EP | 0 301 804 A2 | 2/1989 | ............ | D04H/1/00 |
| EP | 0 301 804 A3 | 5/1990 | ............ | D04H/1/56 |

(Continued)

OTHER PUBLICATIONS

English Translation of Abstract and Claims 1–10 of JP 11–93073A, Kao Corporation (2 pages).

*Primary Examiner*—Sam Chuan Yao
(74) *Attorney, Agent, or Firm*—Pauley Petersen & Erickson

(57) ABSTRACT

A process for forming an absorbent fibrous web composite includes the initial step of forming a fibrous web from hydrophilic fibers and, optionally, thermoplastic fibers. Then, a superabsorbent polymer is completely formed in situ on or in the fibrous web by adding one or more superabsorbent polymer precursor compositions to the fibrous web using a non-contact process, and performing the polymerization reaction(s) completely on or in the web.

24 Claims, No Drawings

FOREIGN PATENT DOCUMENTS

| | | | | |
|---|---|---|---|---|
| EP | 0 390 513 A2 | 10/1990 | ........... | A61L/15/00 |
| EP | 0 402 650 A2 | 12/1990 | ........... | A61L/15/22 |
| EP | 0 390 513 A3 | 8/1991 | ........... | A61L/15/00 |
| EP | 0 402 650 A3 | 11/1991 | ........... | A61L/15/22 |
| EP | 0 223 908 B1 | 2/1993 | ........... | D04H/1/64 |
| EP | 719 531 | 7/1996 | | |
| EP | 729 336 | 6/1998 | | |
| EP | 0 729 366 B1 | 6/1998 | ........... | A61F/13/46 |
| EP | 0 992 250 A2 | 4/2000 | ........... | A61F/15/60 |
| EP | 1 142 696 A1 | 10/2001 | | |
| EP | 1 178 149 A1 | 2/2002 | | |
| WO | WO 95/13777 | 5/1995 | ........... | A61F/13/46 |
| WO | 95/13778 | 5/1995 | | |
| WO | WO 95/13778 | 5/1995 | ........... | A61F/13/46 |
| WO | WO 96/23024 | 8/1996 | | |
| WO | 98/51251 | 11/1998 | | |
| WO | WO 99/34041 | 7/1999 | ............. | D01F/6/36 |
| WO | 00/55418 | 9/2000 | | |
| WO | 01/23177 | 4/2001 | | |
| WO | WO 01/31123 A1 | 5/2001 | .......... | D21H/21/20 |
| WO | WO 01/56625 A2 | 8/2001 | ........... | A61L/15/00 |
| WO | WO 01/56625 A3 | 8/2001 | ........... | A61L/15/00 |
| WO | WO 02/053363 A2 | 7/2002 | ............ | B32B/3/08 |
| WO | WO 03/051253 A1 | 6/2003 | | |
| WO | WO 03/051945 A1 | 6/2003 | | |

* cited by examiner

PROCESS FOR ADDING SUPERABSORBENT TO A PRE-FORMED FIBROUS WEB VIA IN SITU POLYMERIZATION

FIELD OF THE INVENTION

This invention relates to a process for making absorbent material useful in personal care absorbent articles, medical absorbent articles and the like, in which a superabsorbent polymer component of the absorbent material is formed by adding one or more polymer precursor streams containing monomer, catalyst or the like to a pre-formed fibrous web and forming the superabsorbent polymer in situ after the precursor stream(s) contact the web.

BACKGROUND OF THE INVENTION

Processes for making absorbent composite materials having a superabsorbent polymer component are known. In various processes, preformed superabsorbent polymer particles or fibers are combined with cellulose fibers, thermoplastic fibers and the like in a web formation process to make a composite web structure. Illustrative processes are disclosed in U.S. Pat. No. 4,818,464 to Lau, U.S. Pat. No. 4,100,324 to Anderson et al., U.S. Pat. No. 5,350,624 to Georger et al., and U.S. Pat. No. 4,902,559 to Eschwey et al. These processes are commonly referred to as "coform" processes.

Additionally, a process is known where a superabsorbent polymer is only partially formed from a precursor monomer before being added to a fibrous substrate, and the polymerization is completed after the partially polymerized monomer contacts the substrate. U.S. Pat. No. 5,962,068 to Tsuchiya et al. discloses a water-absorptive composite including a fibrous substrate and water-absorptive polymer particles. The water-absorptive polymer is partially polymerized with the aid of a redox initiator before being added to the fibrous substrate. The partially polymerized material is added in a dropwise fashion to the substrate, and the polymerization reaction then proceeds to completion.

One feature that the known processes have in common, is that they require at least some separate process steps for polymerizing or partially polymerizing the superabsorbent material before it can be added to the fibrous substrate. In other words, neither process totally forms the superabsorbent polymer within the fibrous substrate.

DEFINITIONS

The term "cellulose fibers" refers to fibers from natural sources such as woody and non-woody plants, regenerated cellulose, and the derivatives from these fibers by means of chemical, mechanical, or thermal treatment, or any combination of these. Woody plants include, for example, deciduous and coniferous trees. Non-woody plants include, for instance, cotton, flax, esparto grass, milkweed, straw, jute hemp, and bagasse. Regenerated cellulose fibers include, for instance, viscose and rayon. The cellulose derivatives include, for instance, microcrystalline cellulose, chemically crosslinked fibers, and chemically uncrosslinked, twisted fibers.

The term "average pulp fiber length" refers to a weighted average length of pulp determined using a Kajaani fiber analyzer Model No. FS-100 available from Kajaani Oy Electronics in Kajaani, Finland. Under the test procedure, a fiber sample is treated with a macerating liquid to ensure that no fiber bundles or shives are present. Each fiber sample is dispersed in hot water and diluted to about a 0.001% concentration. Individual test samples are drawn in approximately 50 to 500 ml portions from the dilute solution and tested using the standard Kajaani fiber analysis procedure. The weighted average fiber lengths may be expressed by the following equation:

$$\sum_{X_i>0}^{k} (X_i * n_i)/n$$

where
  k=maximum fiber length,
  $X_i$=individual fiber length,
  $n_i$=number of fibers having length $X_i$ and
  n=total number of fibers measured.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

The term "staple filaments or fibers" means filaments or fibers which are natural or which are cut from a manufactured filament prior to forming into a web, and which have a length ranging from about 0.1–15 cm, more commonly about 0.2–7 cm.

The term "substantially continuous filaments or fibers" refers to filaments or fibers prepared by extrusion from a spinnerette, including without limitation spunbonded and meltblown fibers, which are not cut from their original length prior to being formed into a fibrous web. Substantially continuous filaments or fibers may have lengths ranging from greater than about 15 cm to more than one meter; and up to the length of the fibrous web being formed. The definition of "substantially continuous filaments or fibers" includes those which are not cut prior to being formed into a fibrous web, but which are later cut when the fibrous web is cut.

The term "nonwoven web" means a web having a structure of individual fibers or filaments which are interlaid, but not in an identifiable manner as in a knitted fabric. "Fibrous" webs include nonwoven webs as well as fibrous webs where the fibers are interlaid in an identifiable (e.g. regular) manner. The terms "fiber" and "filament" are used herein interchangeably. Nonwoven webs have been formed from many processes such as, for example, meltblowing processes, spunbonding processes, air laying processes, and bonded carded web processes. The term also includes films that have been perforated or otherwise treated to allow air to pass through. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "polymer" generally includes but is not limited to, homopolymers, copolymers, including block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

The term "wettable" and/or "hydrophilic" is meant to refer to a fiber which exhibits a liquid such as water, synthetic urine, or a 0.9 weight percent aqueous saline solution, in air contact angle of less than 90°. The contact angle may be determined, for example, in accordance with ASTM D724-89.

The term "thermoplastic" is meant to describe a material that softens and flows when exposed to heat and which substantially returns to its original hardened condition when cooled to room temperature.

The term "superabsorbent polymer precursor composition" refers to any and all solutions which, when mixed, chemically react to form a superabsorbent polymer. Each solution may be comprised of any combination of oligomer(s), monomer(s), crosslinking reagent(s), neutralizing agent, or initiator(s). In instances when only a single solution is utilized all the desired components must be in said solution and the initiator(s) must require a later activation step (e.g. heating or irradiation). In instances when two or more solutions are utilized the initiator(s) is most often, but not limited to, a chemical redox pair. When a redox pair, comprised of an oxidizing radical generator and a reducing agent, is used as the initiator the oxidizing radical generator and reducing agent must be in separate solutions. The solution of oxidizing radical generator or reducing agent may also contain any combination of oligomer(s), monomer(s), crosslinking reagent(s), or neutralizing agent.

The terms "elastic" and "elastomeric" are used interchangeably to mean a material that is generally capable of recovering its shape after deformation when the deforming force is removed. Specifically, as used herein, elastic or elastomeric is meant to be that property of any material which upon application of a biasing force, permits that material to be stretchable to a stretched biased length which is at least about 50 percent greater than its relaxed unbiased length, and that will cause the material to recover at least 40 percent of its elongation upon release of the stretching elongating force. A hypothetical example which would satisfy this definition of an elastomeric material would be a one (1) inch sample of a material which is elongatable to at least 1.50 inches and which, upon being elongated to 1.50 inches and released, will recover to a length of not more than 1.30 inches. Many elastic materials may be stretched by much more than 50 percent of their relaxed length, and many of these will recover to substantially their original relaxed length upon release of the stretching, elongating force.

The term "recover" or "retract" relates to a contraction of a stretched material upon termination of a biasing force following stretching of the material by application of the biasing force.

The term "superabsorbent material" refers to a water swellable, water-insoluble organic or inorganic material capable, under the most favorable conditions, of absorbing at least about 15 times its weight, preferably at least about 20 times its weight in an aqueous solution containing 0.9% by weight sodium chloride. The term "absorbent material" refers to any material capable of absorbing from about 5 to less than about 15 times its weight of the same solution.

The term "personal care absorbent article" includes diapers, training pants, swim wear, absorbent underpants, adult incontinence products, feminine hygiene products, and the like.

The term "medical absorbent article" includes medical absorbent garments, drapes, gowns, bandages, wipes, and the like.

The term "tissue and towel article" includes facial and bathroom tissues, paper towels, wet wipes, and the like.

SUMMARY OF THE INVENTION

The present invention is directed to a process for making an absorbent fibrous web composite in which a fibrous web is initially formed from absorbent and/or other hydrophilic fibers and, optionally, thermoplastic fibers. Then, a superabsorbent polymer is completely formed in situ in the fibrous web by adding one or more superabsorbent polymer precursor compositions to the fibrous web, and performing the polymerization reaction(s) completely on and/or in the fibrous web.

The process includes the steps of providing a fibrous web including absorbent and/or other hydrophilic fibers and, optionally, thermoplastic fibers and other ingredients. At least one and, desirably two superabsorbent polymer precursor compositions are provided. If only one superabsorbent polymer precursor composition is provided, then it must contain all of the ingredients (monomer, catalyst and the like) necessary to perform the chemical reaction. If two superabsorbent polymer precursor compositions are provided, one of them may include monomer and the other may include a polymerization initiator. Alternatively, each precursor composition may contain a corresponding component of a chemical redox pair (an oxidizing radical generator and a reducing agent) and, in addition, one or both precursor compositions may also include any combination of oligomer(s), monomer(s), crosslinking reagent(s), and/or neutralizing agent(s). In at least the latter the polymerization reaction proceeds spontaneously, beginning when the two precursor compositions are combined.

The superabsorbent polymer precursor composition(s) are added to the fibrous web using a non-contact process. Suitable non-contact processes include dropwise addition, spraying, dipping and the like but do not include embossing, gravure printing or other processes involving contact between the fibrous web and a machine. If two superabsorbent polymer precursor compositions are employed, they may be added separately, so that they first contact each other on or in the fibrous web. The precursor composition(s) and process conditions are selected so that the polymerization reaction for making superabsorbent polymer proceeds entirely on or in the fibrous web.

As a result, the superabsorbent polymer(s) are formed directly onto the surfaces of fibers. The resulting absorbent fibrous web composite has a controlled, stable composition in which the superabsorbent polymer sticks to the fibers and does not migrate within or away from the fibrous web composite.

Additional surface crosslinking may also be performed on the superabsorbent material once the initial polymerization has taken place. The surface crosslinking may enhance the absorbent properties of the material.

DETAILED DESCRIPTION OF THE PRESENTLY PREFERRED EMBODIMENTS

In accordance with the invention, a pre-formed web of fibers is provided. The web may be a nonwoven web, for instance, and contains about 25–100% by weight of absorbent and/or other hydrophilic fibers and about 0–75% by weight of thermoplastic fibers, suitably about 50–100% by weight absorbent and/or other hydrophilic fibers and about 0–50% by weight thermoplastic fibers, desirably about 60–90% by weight absorbent and/or other hydrophilic fibers and about 10–40% by weight thermoplastic fibers. The starting fibrous web may be formed using any conventional technique.

Desirably, the hydrophilic fibers include cellulose fibers. Examples of cellulose fibers include without limitation wood pulp fibers, wood pulp fluff, curled pulp fibers, microcrystalline cellulose, microfibrillar cellulose, cotton, and the like. Other hydrophilic fibers may also be employed, as well as absorbent staple fibers. Pre-formed superabsorbent particles or fibers may also be included. However, for purposes of the invention, at least some superabsorbent polymer must be formed in situ as described below.

When thermoplastic fibers are employed, they may include meltblown fibers. The meltblown fibers may be formed from thermoplastic polymers including, without limitation, polyolefins, polyamides, polyester, polyurethane, polyvinyl alcohol, polycaprolactone, styrene butadiene block copolymers or the like. Suitable polyolefins include without limitation polyethylene, polypropylene, polybutylene, copolymers of ethylene with other alpha-olefins, copolymers of propylene with other alpha-olefins, copolymers of butylene with other alpha-olefins, and combinations thereof. Processes for forming absorbent nonwoven webs containing hydrophilic fibers, meltblown fibers, and other optional ingredients are disclosed in U.S. Pat. No. 5,350,624 to Georger et al., U.S. Pat. No. 4,818,464 to Lau; and U.S. Pat. No. 4,100,324 to Anderson et al.; the disclosures of which are incorporated by reference.

When thermoplastic polymers are employed, they may include spunbond fibers formed from any of the thermoplastic polymers listed above as being useful for meltblown fibers. A process for forming absorbent nonwoven webs containing hydrophilic fibers, spunbond fibers, and other optional ingredients is disclosed in U.S. Pat. No. 4,902,559 to Eschwey et al., the disclosure of which is incorporated by reference.

In accordance with the invention, one or more superabsorbent polymer precursor compositions are added to the fibrous web, and chemically reacted (polymerized) after addition to the fibrous web to make the absorbent fibrous web composite. The superabsorbent polymer precursor composition(s) are added using a non-contact process, such as dripping, spraying, dipping or non-contact printing, in which there is no contact between the fibrous web and equipment which applies the precursor composition(s). Suitable non-contact printing processes for applying the superabsorbent polymer precursor composition(s) are disclosed in U.S. Pat. No. 6,024,438 to Koike et al., U.S. Pat. No. 6,019,457 to Silverbrook, and U.S. Pat. No. 5,875,967 to Ruth, III, which are incorporated by reference. Desirably, the superabsorbent polymer precursor composition(s) are applied as droplets or microdroplets, having a diameter of about 10–1000 microns, desirably 50–500 microns. The microdroplets may have a viscosity of about 5–1000 centipoise, suitably about 10–500 centipoise, desirably about 20–100 centipoise at the application temperature (typically, room temperature).

If only a single superabsorbent polymer precursor composition is employed, it must include all of the reactants (monomer, catalyst, etc.) used to make a superabsorbent polymer. Thus, for purposes of the invention, the use of only one precursor composition is limited to situations where the chemical reaction can be delayed until the precursor composition contacts the fibrous web, including instances where a positive activation step (e.g., via heat, radiation or the like) is needed to initiate the chemical reaction. The use of at least two superabsorbent polymer precursor compositions which spontaneously react only when they contact each other, is desirable for purposes of the invention. This is because the two superabsorbent polymer precursor compositions can be maintained separately, and applied separately using different spraying or dipping nozzles or the like, so that they initially contact each other only when they are both present on or in the fibrous web.

A wide variety of superabsorbent polymer precursor compositions may be employed in the process of the invention. At least one polymer composition may include a monomer. Suitable superabsorbent-forming monomers include the following monomers and combinations thereof:

1. Carboxyl group-containing monomers: monoethylenically unsaturated mono or poly-carboxylic acids, such as (meth)acrylic acid (meaning acrylic acid or methacrylic acid. Similar notations are used hereinafter), maleic acid, fumaric acid, crotonic acid, sorbic acid, itaconic acid, and cinnamic acid;

2. Carboxylic acid anhydride group-containing monomers: monoethylenically unsaturated polycarboxylic acid anhydrides (such as maleic anhydride);

3. Carboxylic acid salt-containing monomers: water-soluble salts (alkali metal salts, ammonium salts, amine salts, etc.) of monoethylenically unsaturated mono- or poly-carboxylic acids (such as sodium (meth)acrylate, trimethylamine (meth)acrylate, triethanolamine (meth)acrylate, sodium maleate, methylamine maleatel;

4. Sulfonic acid group-containing monomers: aliphatic or aromatic vinyl sulfonic acids (such as vinylsulfonic acid, allyl sulfonic acid, vinyltoluenesulfonic acid, stryrene sulfonic acid), (meth)acrylic sulfonic acids [such as sulfopropyl (meth)acrylate, 2-hydroxy-3-(meth)acryloxy propyl sulfonic acid];

5. Sulfonic acid salt group-containing monomers: alkali metal salts, ammonium salts, amine salts of sulfonic acid group containing monomers as mentioned above;

6. Hydroxyl group-containing monomers: monoethylenically unsaturated alcohols [such as (meth)allyl alcohol], monoethylenically unsaturated ethers or esters of polyols (alkylene glycols, glycerol, polyoxyalkylene polyols), such as hydroxethyl (meth)acrylate, hydroxypropyl (meth) acrylate, triethylene glycol (meth)acrylate, poly (oxyethylene oxypropylene) glycol mono (meth)allyl ether (in which hydroxyl groups may be etherified or esterified);

7. Amide group-containing monomers: vinylformamide, (meth)acrylamide, N-alkyl (meth)acrylamides (such as N-methylacrylamide, N-hexylacrylamide), N,N-dialkyl (meth)acryl amides (such as N,N-dimethylacrylamide, N,N-di-n-propylacrylamide), N-hydroxyalkyl (meth)acrylamides [such as N-methylol (meth)acrylamide, N-hydroxyethyl (meth)acrylamide, N,N-dihydroxyalkyl (meth)acrylamides [such as N,N-dihydroxyethyl (meth)acrylamide, vinyl lactams (such as N-vinylpyrrolidone);

8. Amino group-containing monomers: amino group-containing esters (e.g., dialkylaminoalkyl esters, dihydroxyalkylaminoalkyl esters, morpholinoalkyl esters, etc.) of monoethylenically unsaturated mono- or di-carboxylic acid [such as dimethylaminoethyl (meth)acrylate, diethylaminoethyl (meth)acrylate, morpholinoethyl (meth)acrylate, dimethyl aminoethyl fumarate, heterocyclic vinyl compounds such as vinyl pyridines (e.g., 2-vinyl pyridine, 4-vinyl pyridine, N-vinyl pyridine), N-vinyl imidazole; and 9. Quaternary ammonium salt group-containing monomers: N,N,N-trialkyl-N-(meth)acryloyloxyalkylammonium salts [such as N,N,N-trimethyl-N-(meth)acryloyloxyalkylammonium chloride, N,N,N-triethyl-N (meth)acryloyloloxyethylamonnium chloride, 2-hydroxy-3-(meth)-acryloyloxypropyl trimethyl ammonium chloride].

10. Ether-group containing monomers: methoxy polyethylene glycol (meth)acrylate; polyethylene glycol dimethacylate.

Desirably, superabsorbent forming monomers suitable for the process of the invention include without limitation aliphatic unsaturated monocarboxylic acids or salts thereof; specifically unsaturated monocarboxylic acids or salts thereof such as acrylic acid or salts thereof, methacrylic acid or salts thereof, or unsaturated dicarboxylic acids or salts thereof such as maleic acid or salts thereof, itaconic acid or salts thereof, which may be used alone or in combination.

Among these, acrylic acid or salts thereof and methacrylic acid or salts thereof are preferred, with especially preferred being acrylic acid or salts thereof.

Polymerizable monomers giving a water-absorbing polymer in the present invention are preferably aliphatic unsaturated carboxylic acids or salts thereof as described above, therefore, aqueous solutions of these polymerizable monomers are preferably aqueous solutions essentially containing an aliphatic unsaturated carboxylic acid or a salt thereof. As used here, the expression "essentially containing an aliphatic unsaturated carboxylic acid or a salt thereof" means that the aliphatic unsaturated carboxylic acid or a salt thereof is contained at 50 mol % or more, preferably 80 mol % or more on the basis of the total amount of the polymerizable monomer.

Suitable salts of aliphatic unsaturated carboxylic acids normally include water-soluble salts such as alkali metal salts, alkali earth metal salts, ammonium salts or the like. The neutrality is appropriately selected depending on the purpose, but 20–90 mol % of carboxyl group is preferably neutralized with an alkali metal salt or an ammonium salt in the case of acrylic acid. If the partial neutrality of an acrylic monomer is less than 20 mol %, the resulting water-absorbing polymer tends to have low water-absorbing capacity.

Acrylic monomers can be neutralized with alkali metal hydroxides or bicarbonates or ammonium hydroxide or the like, preferably alkali metal hydroxides such as sodium hydroxide and potassium hydroxide.

Superabsorbent-forming monomers may also include comonomers which are polymerizable along with any of the monomers listed above. The comonomers may form part of the same superabsorbent polymer precursor composition as the primary monomer, or may be part of a different superabsorbent polymer precursor composition, and may be added to the fibrous mixture using the same or different streams. Where the primary monomer is an aliphatic unsaturated carboxylic acid, suitable comonomers include without limitation secondary monomers such as (meth)acrylamide, (poly)ethylene glycol (meth)acrylate, 2-hydroxyethyl (meth)acrylate or even slightly water-soluble monomers including acrylate capped urethanes, acrylic alkyl esters such as methyl acrylate or ethyl acrylate may also be copolymerized in an amount within a range that does not affect performance of the resulting water-absorbing polymers in the present invention. As used herein, the term "(meth)acryl" means both "acryl" and "methacryl."

Aliphatic unsaturated carboxylic acids or salts thereof, especially acrylic acid or salts thereof sometimes form a self-crosslinked polymer by themselves, but may be positively induced to form a crosslinked structure using a crosslinker. The use of a crosslinker normally improves water-absorbing performance of the resulting water-absorbing polymer. Preferably, suitable crosslinkers include divinyl compounds copolymerizable with said polymerizable monomers such as N,N'-methlenebis(meth)acrylamide, (poly)ethylene glycol di(meth)acrylate and water-soluble compounds having two or more functional groups capable of reacting with a carboxylic acid including polyglycidyl ethers such as ethylene glycol diglycidyl ether, polyethylene glycol diglycidyl ether. Among them, N,N'-methlenebis(meth)acrylamide is especially preferred. Crosslinkers are used in an amount of 0.001–1% by weight, preferably 0.01–0.5% by weight on the basis of the amount of the monomer, and may be added in the same superabsorbent polymer precursor composition as the monomer, or as part of a different precursor composition.

The concentration of polymerizable monomers in an aqueous polymerizable monomer solution essentially containing an aliphatic unsaturated carboxylic acid or a salt thereof as described above is 20% or more, preferably 25% or more. Concentrations less than 20% by weight are not preferred because droplets having an appropriate viscosity are difficult to produce whereby the resulting water-absorbing polymer has insufficient water-absorbing capacity. The upper limit is preferably about 80% by weight in respect of handling of the polymerization reaction solution.

One or more polymerization initiators may be added in the same or a different superabsorbent polymer precursor composition as the monomer(s). The polymerization initiator may be added as part of the same precursor composition as the monomer if subsequent activation is required or if the initiator is a single component of a redox pair. Alternatively, the polymerization initiators may be added as part of a different precursor composition as the monomer due to the fact that the polymerization initiators may act quickly to polymerize the monomer units once contact is made. When the monomer and polymerization initiator make initial contact in the fibrous web, the polymerization reaction is initiated, and occurs entirely within the fibrous web.

Polymerization initiators suitable for the present invention include without limitation somewhat water-soluble redox systems combining an oxidizing radical generator and a reducing agent. Such oxidizing agents include hydrogen peroxide, potassium bromate, N-bromosuccinimide, persulfates such as ammonium persulfate, sodium persulfate, or potassium persulfate, peroxides including hydroperoxides such as 1-butyl hydroperoxide or cumene hydroperoxide, secondary cerium salts, permanganates, chlorites, hypochlorites, etc., among which hydrogen peroxide is especially preferred. These oxidizing agents may be used in an amount of 0.001–10% by weight, desirably 0.01–2% by weight on the basis of polymerizable monomers.

Reducing agents are also used with the redox system, and may be added as part of the polymerization initiator. Suitable reducing agents are capable of forming a redox system with said oxidizing agents, specifically sulfites such as sodium sulfite or sodium hydrogensulfite, sodium thiosulfate, cobalt acetate, copper sulfate, ferrous sulfate, ferrous ammonium sulfate, sodium metabisulfite, tertiary amines or diamines, L-ascorbic acid or L-ascorbic acid alkali metal salts, etc. Among others, L-ascorbic acid or L-ascorbic acid alkali metal salts are especially preferred. These reducing agents are used in an amount of 0.001–10% by weight, preferably 0.01–2% by weight on the basis of polymerizable monomers. Desirably, the precursor composition containing the oxidizing radical generator is added using a different addition stream than is used for the reducing agents.

Process conditions, feed rates, and the like should be tailored to produce the desired composition for the absorbent fibrous web composite. The process conditions and feed rates may be tailored to produce an absorbent fibrous web composite having the following compositions:

| | Composition, % By Weight | | |
|---|---|---|---|
| | Hydrophilic Fibers | Superabsorbent Polymer Formed In Situ | Thermoplastic Fibers |
| Broad | 25–99 | 1–75 | 0–74 |
| Intermediate | 35–80 | 15–65 | 0–45 |
| Narrow | 40–70 | 20–50 | 10–30 |

Where a redox system of polymerization initiator(s) as described above is employed, the chemical reaction proceeds spontaneously. Otherwise, depending on the mechanism of chemical reaction employed, it may be necessary to raise the temperature of the fibrous web, irradiate it, or employ some other treatment in order to facilitate and optimize the chemical reaction.

Examples of superabsorbent polymers which may be formed in situ include without limitation the alkali metal and ammonium salts of poly(acrylic acid) and poly(methacrylic acid), poly(acrylamides), poly(vinyl ethers), maleic anhydride copolymers with vinyl ethers and alpha-olefins, poly (vinyl pyrrolidone), poly(vinylmorpholinone), poly(vinyl alcohol), and mixtures and copolymers thereof. Further superabsorbent materials (some of which may be formed before addition to the fibrous web) include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Known processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbent materials may be xerogels which form hydrogels when wetted. The term "hydrogel", however, has commonly been used to also refer to both the wetted and unwetted forms of the superabsorbent polymer material. The superabsorbent materials can be in many forms such as flakes, powders, particulates, fibers, continuous fibers, networks, solution spun filaments and webs. The particles can be of any desired shape, for example, spiral or semi-spiral, cubic, rod-like, polyhedral, etc. Needles, flakes, fibers, and combinations may also be used.

Pre-formed superabsorbents are generally available in particle sizes ranging from about 20 to about 1000 microns. Examples of suitable commercially available particulate superabsorbents include HYSORB® P7050 and HYSORB® P7060, available from BASF Corporation, DRYTECH® 2035LD available from Dow Chemical Co. located in Midland, Mich., and FAVOR® SXM 880, available from Stockhausen located in Greensborough, N.C. An example of a fibrous superabsorbent is OASIS® 101, available from Technical Absorbents, located in Grimsby, United Kingdom.

The resulting absorbent composite material includes a plurality of hydrophilic fibers having superabsorbent particles formed in situ which stick to the surfaces of the fibers, and which are not freely movable. Suitably, the superabsorbent particles are formed in situ in such quantity which permits them to be spaced apart from each other by an average distance of about 50–4000 microns, desirably about 200–3000 microns, so that the superabsorbent particles may swell in the presence of liquid without contacting each other. Suitably, the in situ formed superabsorbent particles have the same average diameter in the dry, unswollen state as conventional, pre-formed superabsorbent particles. The average dry particle diameter may range from about 10–1000 microns, desirably about 20–500 microns. A primary advantage of the absorbent composite materials of the invention is that the superabsorbent particles stick to the fibrous substrate, so that the distance between the superabsorbent particles is maintained.

The absorbent composite fibrous material of the invention is useful in a wide variety of absorbent articles, particularly as an absorbent core material in personal care absorbent articles and medical absorbent articles. Personal care absorbent articles include diapers, training pants, swim wear, absorbent underpants, baby wipes, adult incontinence products, feminine hygiene products and the like. Medical absorbent articles include medical absorbent garments, drapes, gowns, bandages, wound dressings, underpads, wipes, and the like.

While the embodiments disclosed herein are presently considered to be preferred, various modifications and improvements can be made without departing from the spirit and scope of the invention. The scope of the invention is indicated by the appended claims, and all changes that fall within the meaning and range of equivalents are intended to be embraced therein.

We claim:

1. A process for making an absorbent composite web, comprising the steps of:
   providing a first superabsorbent polymer precursor composition;
   providing a pre-formed fibrous web including a plurality of absorbent hydrophilic fibers;
   adding the first superabsorbent polymer precursor composition to the fibrous web using a non-contact printing process which is not a spraying process; and
   chemically reacting the first superabsorbent polymer precursor composition on or in the fibrous web to form a superabsorbent polymer consisting essentially of particles which stick to fiber surfaces, have a dry diameter of about 10–1000 microns, and are spaced apart by 50–4000 microns;

wherein the superabsorbent polymer constitutes 20–75% by weight of the absorbent composite.

2. The process of claim 1, wherein the superabsorbent polymer precursor composition is applied as microdroplets having a diameter of about 10–1000 microns.

3. The process of claim 2, wherein the microdroplets have a diameter of about 50–500 microns.

4. The process of claim 2, wherein the microdroplets have a viscosity of about 5–1000 centipoise.

5. The process of claim 2, wherein the microdroplets have a viscosity of about 10–500 centipoise.

6. The process of claim 2, wherein the microdroplets have a viscosity of about 20–100 centipoise.

7. The process of claim 1, further comprising the steps of:
providing a second superabsorbent polymer precursor composition;
adding the second superabsorbent polymer precursor composition to the fibrous web using a non-contact process; and
chemically reacting the first and second superabsorbent polymer precursor compositions together on or in the web to form the superabsorbent polymer.

8. The process of claim 7, wherein the first and second superabsorbent polymer precursor compositions are added separately to the fibrous web.

9. The process of claim 1, wherein the fibrous web further comprises a plurality of thermoplastic fibers.

10. The process of claim 1, wherein the hydrophilic fibers comprise cellulose fibers.

11. The process of claim 1, wherein the hydrophilic fibers comprise staple fibers.

12. A process for making an absorbent web composite, comprising the steps of:
providing a starting web including about 25–100% by weight cellulose fibers and about 0–75% by weight thermoplastic fibers;
providing a first superabsorbent polymer precursor composition;
applying the first superabsorbent polymer precursor composition to the web using a non-contact printing process which is not a spraying process; and
chemically reacting the first superabsorbent polymer precursor composition on or in the web to form a superabsorbent polymer consisting essentially of particles which stick to fiber surfaces, have a dry diameter of about 10–1000 microns, and are spaced apart by 50–4000 microns;
wherein the superabsorbent polymer constitutes 20–75% by weight of the absorbent composite.

13. The process of claim 12, wherein the starting web comprises about 50–100% by weight cellulose fibers and about 0–50% by weight thermoplastic fibers.

14. The process of claim 12, wherein the starting web comprises about 60–90% by weight cellulose fibers and about 10–40% by weight thermoplastic fibers.

15. The process of claim 12, wherein the thermoplastic fibers comprise meltblown fibers.

16. The process of claim 12, wherein the thermoplastic fibers comprise spunbond fibers.

17. The process of claim 12, wherein the superabsorbent polymer comprises a polymer selected from alkali metal and animonium salts of poly(acrylic acid) and poly(methacrylic acid), poly(acrylamides), poly(vinyl ethers), maleic anhydride copolymers with vinyl ethers and alpha-olefins, poly (vinyl pyrrolidone), poly(vinyl morpholinone), poly(vinyl alcohol), and combinations thereof.

18. The process of claim 12, wherein the absorbent web composite comprises about 1–75% by weight of the superabsorbent polymer.

19. The process of claim 12, wherein the absorbent web composite comprises about 15–65% by weight of the superabsorbent polymer.

20. The process of claim 12, wherein the absorbent web composite comprises about 20–50% by weight of the superabsorbent polymer.

21. A process for making an absorbent web composite, comprising the steps of:
providing a first superabsorbent polymer precursor composition including a monomer;
providing a second superabsorbent polymer precursor composition including a polymerization initiator;
providing a pre-formed fibrous web including a plurality of cellulose fibers;
adding the first superabsorbent polymer precursor composition to the fibrous web using a non-contact printing process which is not a spraying process;
separately adding the second superabsorbent polymer precursor composition to the fibrous web using a non-contact printing process; and
chemically reacting the first and second polymer precursor compositions on or in the fibrous web to form a superabsorbent polymer consisting essentially of particles which stick to fiber surfaces, have a dry diameter of about 10–1000 microns, and are spaced apart by 50–4000 microns;
wherein the superabsorbent polymer constitutes 20–75% by weight of the absorbent composite.

22. The process of claim 21, wherein the polymerization initiator comprises a redox system.

23. The process of claim 21, wherein the monomer comprises a compound selected from the group consisting of aliphatic unsaturated monocarboxylic acids and their salts, methacrylic acids and their salts, unsaturated dicarboxylic acids and their salts, and combinations thereof.

24. The process of claim 21, wherein the monomer comprises a compound selected from the group consisting of acrylic acid and its salts, methacrylic acid and its salts, and combinations thereof.

* * * * *